(12) United States Patent
Buehring et al.

(10) Patent No.: US 7,659,116 B2
(45) Date of Patent: Feb. 9, 2010

(54) MONOCLONAL ANTIBODY AGAINST FRIZZLED RECEPTOR 4

(75) Inventors: Hans-Joerg Buehring, Tuebingen (DE); Sigrid Hojak, Berlin (DE); Ingrid Albert, Tuebingen (DE)

(73) Assignee: Eberhard-Karls-Universitaet Tuebingen Universitaetsklinikum, Tuebingen (DE)

( * ) Notice: Subject to any disclaimer, the term of this patent is extended or adjusted under 35 U.S.C. 154(b) by 217 days.

(21) Appl. No.: 11/787,023

(22) Filed: Apr. 12, 2007

(65) Prior Publication Data

US 2008/0038272 A1 Feb. 14, 2008

Related U.S. Application Data

(63) Continuation of application No. PCT/EP2005/011035, filed on Oct. 13, 2005.

(30) Foreign Application Priority Data

Oct. 13, 2004 (DE) .................... 10 2004 050 620

(51) Int. Cl.
| | |
|---|---|
| C12N 5/16 | (2006.01) |
| C12N 5/18 | (2006.01) |
| C07K 14/705 | (2006.01) |
| C07K 16/28 | (2006.01) |
| G01N 33/53 | (2006.01) |
| G01N 33/567 | (2006.01) |

(52) U.S. Cl. ............... 435/334; 530/388.1; 530/388.22; 530/391.1; 530/391.7; 435/7.1; 435/7.21

(58) Field of Classification Search ................. None
See application file for complete search history.

(56) References Cited

U.S. PATENT DOCUMENTS

| 7,238,780 B2 * | 7/2007 | Ahmad et al. |
| 2005/0214872 A1 | 9/2005 | Buehring et al. |
| 2007/0116701 A1 * | 5/2007 | Gurney et al. |

FOREIGN PATENT DOCUMENTS

| CA | 2343574 | 3/2000 |
| DE | 19846979 | 3/2000 |
| DE | 19856066 | 6/2000 |
| DE | 69726884 | 6/2004 |
| EP | 1001023 | 5/2000 |
| EP | 0954580 | 12/2003 |
| JP | 2004051557 | 2/2004 |
| WO | WO-99/26960 | 6/1999 |
| WO | WO-02/088081 | 11/2002 |
| WO | WO-03/005034 | 1/2003 |
| WO | WO-2004/020668 | 3/2004 |

OTHER PUBLICATIONS

Kirikoshi et al., Molecular cloning and characterization of human Frizzled-4 on chromosome 11a14-q21, Biochem. Biophys. Res. Comm. 264:955-961, 1999.*
Holcombe et al., J. Clin. Pathol. (2002) 55(4):220-226.
Huelsken et al., J. Cell Sci. (2002) 115:3977-3978.
International Search Report for PCT/EP2005/011035, mailed on Feb. 16, 2006, 3 pages.
Karim et al., Pathology (2004) 36(2):120-128.
Kohler et al., Nature (1975) 256(5517):495-497.
Malbon, Front. Biosci. (2004) 9:1048-1058.
Niehrs, Developmental Cell (2004) 6(4):453-454.
Pubmed Abstract, Int J. Oncol. (Oct. 2001) 19(4): 767-771.
Raay et al., Dev. Genes Evol. (2001) 211(8-9): 453-457.
Robitaille et al., Nat. Genet. (2002) 32(2): 326-330.
Sen et al., Arthritis Rheum. (2001) 44(4): 772-781.
Translation of International Preliminary Report on Patentability for PCT/EP2005/011035, date issued on Apr. 24, 2007, 12 pages.
Xu et al., Cell (2004) 116(6): 883-895.

* cited by examiner

*Primary Examiner*—Elizabeth C. Kemmerer
*Assistant Examiner*—Claire Kaufman
(74) *Attorney, Agent, or Firm*—Morrison & Foerster LLP (57) ABSTRACT

The present invention relates to a monoclonal antibody or fragment thereof, which binds specifically and/or selectively to human receptors of the Frizzled (FZD) family. It further relates to a hybridoma cell that produces the antibody according to the invention. Another object of the present invention is a method for the detection and/or isolation of receptors of the FZD family or homologs or fragments thereof in a biological sample and a method for the identification and/or isolation of biological material comprising or expressing receptors of the FZD family or homologs or fragments thereof. The invention further relates to the use of the antibody according to the invention or fragments thereof for the specific and/or selective detection and/or isolation of receptors of the FZD family, a composition comprising the monoclonal antibody according to the invention or fragments thereof, and a kit comprising the monoclonal antibody according to the invention or fragments thereof.

8 Claims, 6 Drawing Sheets

MONOCLONAL ANTIBODY AGAINST FRIZZLED RECEPTOR 4

CROSS-REFERENCE TO RELATED APPLICATIONS

This application is a continuation of copending International Patent Application PCT/EP2005/011035 filed on Oct. 13, 2005 and designating the United States, which was not published under PCT Article 21(2) in English, and claims priority of German Patent Application DE 10 2004 050 620.5 filed on Oct. 13, 2004. The contents of the above-referenced applications are incorporated herein by this reference in their entirety.

BACKGROUND OF THE INVENTION

1. Field of the Invention

The present invention relates to a monoclonal antibody or fragment thereof, which binds specifically and/or selectively to human receptors of the Frizzled (FZD) family. It further relates to a hybridoma cell, which produces the antibody according to the invention. A further object of the present invention is a method for the detection and/or isolation of receptors of the FZD family or homologs or fragments thereof in a biological sample and a method for the identification and/or isolation of biological material that has or expresses receptors of the FZD family or homologs or fragments thereof. The invention further relates to the use of the antibody according to the invention or fragments thereof for the specific and/or selective detection and/or isolation of receptors of the FZD family, a composition comprising the monoclonal antibody according to the invention or fragments thereof, and a kit that comprises the monoclonal antibody according to the invention or fragments thereof.

2. Related Prior Art

Frizzled (FZD) receptors are proteins of the 7-transmembrane type, which have a sequence motif with seven α-helical domains, by means of which anchoring in the membrane takes place. This motif is typical for the so-called G protein-coupled receptors (GPCRs). Many authors therefore also include the Frizzled receptors in the GPCR superfamily; cf. for example Malbon C. C. (2004), "Frizzleds: new members of the superfamily of G-protein-coupled receptors", *Front. Biosci.*, Vol. 9, pages 1048 to 1058. Furthermore, the Frizzled receptors have a cysteine-rich domain (CRD) at their amino-terminal end.

Frizzled receptors are important components of the so-called Wnt (wingless-type) signal pathway, which is conserved both in vertebrates and in invertebrates. The most important ligands of the Frizzled receptors are the Wnt proteins, which induce intracellular events by binding to the extracellular portion of the Frizzled receptor. In addition to the FZD receptors, members of another class of cell surface receptors from the family of LDL-receptor-related proteins (LRP) are involved in the reception and transmission of Wnt signals.

Intracellular signal transduction can essentially take place by two different pathways. Ligands of the Wnt5A class stimulate signal transduction via the pertussis-toxin-sensitive group of heterotrimeric G proteins through the increase in the intracellular $Ca^{2+}$ concentration and via the RhoA/c-jun-N-terminal kinase signal cascade (called the Wnt-$Ca^{2+}$ pathway). With ligands of the Wnt1 class, in contrast, signal transduction takes place via another important intracellular signal protein, β-catenin (called the Wnt/β-catenin pathway). β-Catenin is a transcription activator. In the absence of a Wnt signal, a portion of the intracellular β-catenin is bound to the cytosolic tail of the so-called cadherin protein and another portion of the cytosolic β-catenin is located in a complex of the proteins axin, APC (adenomatous polyposis coli) and GSK-3β (glycogen synthase kinase-3). In this so-called degradation complex, β-catenin is phosphorylated by GSK-3β and so triggers its own ubiquitinylation and therefore degradation in proteasomes. Accordingly, in the absence of Wnt, β-catenin is unstable and cannot perform its function as a transcription activator. In the absence of Wnt, therefore, various Wnt-regulated genes are inactivated, which is ensured by a corepressor protein with the designation Groucho, which together with the transcription-regulating proteins LEF-1/TCF is bound to the DNA in the promoter region of these genes.

When Wnt binds to the Frizzled receptor and its receptor LRP, through an as yet unknown mechanism there is activation of the intracellular protein Dishevelled. Activated Dishevelled induces, again by an as yet unknown mechanism, the inactivation of GSK-3β in the degradation complex. As a result there is inhibition of the phosphorylation and degradation of β-catenin. β-Catenin is then stable and accumulates in the cytoplasm and in the nucleus. In the nucleus, β-catenin binds to LEF-1/TCF (lymphoid enhancer factor-1/T cell-specific factor), releases the Groucho factor and thus stimulates the transcription of Wnt-regulated genes. A review of the Wnt signal pathway is given for example in Huelsken J. and Behrens J. (2002), "The Wnt signalling pathway", *J. Cell Sci.*, Vol. 115, pages 3977 to 3978.

In addition to Wnt, another ligand for Frizzled receptors was found recently, which has the name Norrin; cf. Niehrs C. (2004), "Norrin and Frizzled: A New Vein for the Eye", *Developmental Cell*, Vol. 6, pages 1 to 20.

Frizzled receptors play an important role in the differentiation and organogenesis of embryonic tissue, in oogenesis and development of the germinal layer and in the autoregeneration of stem cells. Consequently, a great many teams from the area of basic research are involved in the detailed characterization of these receptors.

However, Frizzled receptors also seem to play an important role in many diseases. Thus, these receptors have a key function in carcinogenesis; cf. Holcombe R. F. et al. (2002), "Expression of Wnt ligands and Frizzled receptors in colonic mucosa and in colon carcinoma", *J. Clin. Pathol.*, Vol. 55(4), pages 220 to 226, and Karim R. et al. (2004), "The significance of the Wnt pathway in the pathology of human cancers", *Pathology* 36(2), pages 120 to 128.

In addition, a link was found with Norrie disease, an X-chromosomal-recessive disease characterized by degenerative changes in the retina; cf. Xu et al. (2004), "Vascular development in the retina and inner ear: control by Norrin and Frizzled4, a high-affinity ligand-receptor pair", *Cell*, Vol. 116 (6), pages 883 to 895; involvement of Frizzled receptors in the clinical picture of familial exudative vitreoretinopathy, a progressive disease of the retina; cf. Robitaille et al. (2002), "Mutant frizzled-4 disrupts retinal angiogenesis in familial exudative vitreoretinopathy", *Nat. Genet.*, Vol. 32(2), pages 326 to 330.

Moreover, Frizzled receptors are involved in the clinical picture of rheumatoid arthritis; cf. Sen et al. (2001), "Blockade of Wnt-5A/frizzled 5 signaling inhibits rheumatoid synoviocyte activation", *Arthritis Rheum.*, Vol. 44(4), pages 772 to 781. Furthermore, Frizzled receptors are described in the literature in connection with a great many other clinical pictures.

Against this background, both for research and for diagnostics and pharmaceutics, there is a great need for antibodies that are able to selectively recognize and/or identify Frizzled receptors.

Polyclonal antibodies against various Frizzled receptors are widely described in the state of the art, for example against human FZD-5 (Sen et al., loc. cit.), against mouse FZD-9 (Van Raay et al. (2001), "Frizzled 9 is expressed in neural precursor cells in the developing neural tube", *Dev. Genes Evol.*, Vol. 211(8-9), pages 453 to 457), or against human FZD-1 and FZD-2 (Holcombe R. F. et al., loc. cit.).

Polyclonal antibodies of this kind have the disadvantage that they are not of unlimited availability, and they can no longer be reproduced identically after use. Moreover, polyclonal antibodies naturally comprise a mixture of different antibodies, each directed against different antigenic structures of the particular epitope. Consequently it is not possible, by means of polyclonal antibodies, to identify the same antigenic structure reproducibly again and again.

Another disadvantage of polyclonal antibodies is that they sometimes display very high cross reactivities with other proteins that are not of interest, which greatly restricts their use in immunoblotting or in immunoprecipitation and makes a diagnostic or therapeutic use of this mixture impossible.

There is therefore an increased need for the supply of monoclonal antibodies that are directed against Frizzled receptors, and especially against the human variants. However, it turns out that production of these monoclonal antibodies is particularly difficult, as Frizzled receptors in the animal kingdom are very highly conserved with respect to their amino acid sequence and therefore their three-dimensional structure. It is therefore assumed that it is almost impossible to produce monoclonal antibodies by means of which a species-specific demarcation of the Frizzled receptors is possible.

The company R&D Systems Inc., Minneapolis, Minn., USA, offers monoclonal antibodies against the mouse variant of Frizzled-1 (Clone 162531), -3 (Clone 169310), -4 (Clone 145901) and -7 (Clone 151143). The manufacturer advertises that the respective human variants of the Frizzled receptors could also be detected with these antibodies. However, experts have shown, and the inventors have also verified, that satisfactory detection of the human variants is not possible by means of these antibodies. Rather, binding of these antibodies to human receptors of the Frizzled family is nonspecific and unselective, so that only a certain level of cross reactivity with the human variants combined with high affinity for other unwanted structures can be determined. Therefore it is not possible to use these monoclonal antibodies for selective and/or specific identification of human Frizzled receptors.

SUMMARY OF THE INVENTION

The problem of the present invention is therefore to provide a monoclonal antibody that binds specifically and/or selectively to human receptors of the Frizzled family.

The inventors have now succeeded in solving this problem for the first time. Such a monoclonal antibody has now been made available. Concretely, the inventors were able to produce three monoclonal antibodies, which bind highly specifically and selectively to the human variants of FZD-4, -7 and -9 or -6. These antibodies are produced by hybridoma cells, which were deposited in culture on 15 Jul. 2004 in the Deutsche Sammlung für Mikroorganismen und Zelikulturen (DSMZ; "German Collection for Microorganisms and Cell Cultures"), Mascheroder Weg 1b, 38124 Braunschweig, under numbers DSM ACC2668 (FZD-9 and -6), DSM ACC2669 (FZD-7) and DSM ACC 2667 (FZD-4) in accordance with the Budapest Treaty.

These monoclonal antibodies have surprising and unforeseeable properties. Thus, they bind highly selectively and specifically to the human variants of the Frizzled receptors, and consequently only display extremely slight cross reactivities with the variants of other species. In view of the high degree of conservation of the Frizzled receptors in the animal kingdom, this was unexpected. Rather it had been assumed until now that owing to the structural similarities of the Frizzled receptors, cross reactivities with variants of other species are even more unavoidable.

According to the invention, specific and/or selective binding to human FZD receptors means that the monoclonal antibody was established concretely against a human FZD receptor, but not against a variant of another species, for example the mouse, which would then only have cross reactivity with the human variant.

Within the scope of the present invention, instead of the antibody according to the invention it is also possible to use a fragment thereof. Fragment in this context means any segment of the antibody that retains the antigen binding function of the antibody. Such fragments are for example $F_{ab}$, $F_{(ab')2}$, $F_v$ and other fragments, for example CDR (complementary determining region, hypervariable region) fragments. Said fragments also display the binding specificity of the antibody and can also for example be produced as recombinant proteins by known methods.

The inventors' particular achievement is that the deposited antibodies not only provide a highly selective tool for use in research and medicine, but that by means of these antibodies it is also possible to produce other monoclonal antibodies, which bind to the same antigen. As it was possible, unexpectedly, to produce highly selective antibodies against the human variant of the FZD antibodies, the inventors have cleared an important hurdle and have thus smoothed the way for the development of comparable monoclonal antibodies. It is thus possible for the antigen that is recognized by the deposited antibodies to be isolated and used for the immunization e.g. of mice. The subsequent production of monoclonal antibodies is described in detail in the state of the art; cf. Köhler G. and Milstein C. (1975), "Continuous cultures of fused cells secreting antibody of predefined specificity", *Nature*, Vol. 256(5517), pages 495 to 497, the content of which is herewith incorporated by reference. Then, after immunization with the isolated antigen, the antibody-producing cells are removed from the animals and are fused with an immortalized cell line. From the resultant hybridoma cell lines, one is selected that produces antibodies, in an unlimited quantity, against the antigen that was used for the immunization.

A further object of the present invention therefore also relates to a monoclonal antibody or a fragment thereof that binds to an identical antigen as an antibody that is produced by the hybridoma cells which were deposited in cultures at the DSMZ under numbers DSM ACC2668, DSM ACC2669 and DSM ACC 2667 according to the Budapest Treaty.

The present invention also relates to the antibodies concretely deposited at the DSMZ.

The monoclonal antibody deposited with the number DSM ACC 2667 has the isotype mouse IgG1, which selectively recognizes human FZD-4, but not other receptors of the Frizzled family, e.g. FZD-1, -5, -6, -7, -9 or -10. The monoclonal antibody designated with the number DSM ACC 2669 has the isotype mouse IgG1 and selectively recognizes human FZD-7, but not other receptors of the Frizzled family, such as FZD-1, -4, -5, -6, -9 or -10. The monoclonal antibody with the number DSM ACC 2668 has the isotype mouse IgM and selectively recognizes FZD-9 and FZD-6, but not other receptors from the Frizzled family, for example FZD-1, -4, -5, -7 or -10.

With the antibodies according to the invention, the phenotypes of hematopoietic, mesenchymal and neuronal stein/progenitor cell populations (HSC, MSC, NPC) can be analyzed with respect to their FZD expression. Thus, the inventors have already investigated a large number of different cell types, such as tumor cells of various kinds, including leukemia cells, primary cells and cultivated primary cells. It was found, surprisingly, that the most varied of cells display a characteristic FZD expression spectrum, so that the antibodies according to the invention can therefore be used for isolating these cells from a heterogeneous mixture of cells. For example, with the deposited monoclonal antibody against FZD-4, it is possible, advantageously, to recognize and isolate FZD-4-positive cells, such as neuronal progenitor cells.

A further object of the present invention relates to a monoclonal antibody described above or a fragment thereof, to which a marker and/or a therapeutic active substance is coupled.

According to the invention, a marker means any compound by means of which localization and identification of the antibodies and therefore of the FZD receptors is possible in vitro or in vivo or even in situ. This includes colored indicators, such as dyes, with fluorescent, phosphorescent or chemiluminescent properties, AMPPD, CSPD, radioactive indicators, such as $^{32}P$, $^{35}S$, $^{125}I$, $^{131}I$, $^{14}C$, $^{3}H$, non-radioactive indicators, such as biotin or digoxigenin, alkaline phosphatase or horseradish peroxidase. The marked antibodies are then detected by imaging techniques that are known in the state of the art, such as autoradiography, blotting, hybridization or microscopy techniques.

Any active substance that induces a specific reaction in the organism may be taken into consideration as a therapeutic active substance, for example a medicinal product or even a toxin. In this way an active substance can purposely be brought close to an FZD receptor and can for example act directly on the cell expressing this receptor. This therefore prevents such an active substance getting into regions of an organism or organ in which an action is undesirable.

A further object of the present invention relates to a hybridoma cell, which produces the antibody or antibodies described above.

By means of this hybridoma cell, when it is cultivated, a corresponding antibody that it produces can be obtained in unlimited quantity and can be made available. Within the scope of scientific or diagnostic applications, this therefore ensures reproducibility of the results. This is a prerequisite for approval as a medicinal product.

A further object of the present invention is a method for the detection and/or isolation of human receptors of the FZD family or homologs or fragments thereof in a biological sample, comprising the following steps: (1) preparation of the biological sample; (2) contacting said biological sample with an antibody or a fragment thereof; (3) determination whether specific and/or selective binding to said antibody or said fragment thereof has taken place, and (4.1) correlation of a positive result in step (3) with the detection of a receptor from the FZD family, and/or (4.2) isolation of the antigen in the case of a positive result in step (3), wherein, as antibody of fragment thereof, the antibody described above or the fragment thereof is used.

This method can be used for the targeted detection of human receptors of the FZD family. For this, steps (1), (2), (3) and (4.1) are carried out. With additional execution of step (4.2) after or instead of (4.1), however, it is also possible to isolate the antigen, for example the receptor itself, which can be used for the production of further comparable monoclonal antibodies as pointed out above.

With this method it is also possible to find as yet unknown homologs of the human FZD receptors, meaning, according to the invention, components with extremely similar structures to those of the respective FZD receptors, which in some circumstances have not been described to date.

Moreover, with this method it is possible to obtain large quantities of FZD receptors for subsequent crystallization and structural elucidation. Furthermore, there is the possibility of isolating the FZD receptors with their natural ligands or other factors or molecules interacting with them in large quantities, carrying out co-crystallization of the complexes in order to obtain data on the three-dimensional structure of these complexes. That would create the basis for example for the development of specific substances that interact with FZD receptors (drug design), which have the correct three-dimensional shape.

The biological sample can be cells, cell cultures, cell fragments, tissues, protein concentrates or other solutions or suspensions containing biological material, or which are to be investigated for the presence of biological material.

The method can be carried out in a suitable buffer system, for which e.g. Tris, Good or phosphate buffers are used. The contacting or incubation in step (2) is then carried out with shaking if necessary, according to commonly known biochemical techniques.

The determination in step (3) is carried out using methods that are commonly known in the state of the art, such as immunoblotting, immunoprecipitation or other immunological techniques.

Using such a method, it is also possible within the scope of basic research for the human variants of the FZD receptors to be characterized in greater detail with respect to their as yet largely unknown biochemical mechanism of action. Thus, the receptors or fragments thereof can for example be crystallized after isolation and their three-dimensional structure can be elucidated. In this connection, for example using the technique of rational drug design, it is then possible to purposely construct active substances that bind selectively to the FZD receptors. The method according to the invention accordingly provides a technique that represents a first step for a better understanding of the FZD receptors and for the development of a targeted active substance.

A further object of the present invention is a method for the identification of biological material with respect to the presence and/or expression of receptors of the FZD family or homologs or fragments thereof and optionally for the isolation of such a material, comprising the following steps: (1) provision of said biological material; (2) contacting said biological material with an antibody or fragment thereof; (3) determination whether specific and/or selective binding to said antibody or said fragment thereof has taken place, and (4.1) correlation of a positive result in step (3) with the identification of the presence or of the expression of receptors of the FZD family or homologs or fragments thereof in or on the biological material, and optionally (4.2) isolation of the binding partner in the case of a positive result in step (3), wherein, as antibody or fragment thereof, the antibody described above or the fragment thereof is used.

This method is modified, relative to the method described previously, in that biological material, for example cells such as stem cells, cell fragments etc., can be identified with respect to their phenotype with reference to FZD expression, and isolated.

Against this background, the present invention also relates to the use of the antibody according to the invention for specific and/or selective detection and/or isolation of receptors of the FZD family, preferably for analysis of the carcinogenesis and/or differentiation and organogenesis of embryonic tissue and/or oogenesis and development of the germ layer and/or autoregeneration of stem cells.

A further object is a composition, preferably a pharmaceutical composition, comprising the antibody according to the invention or fragments thereof, and preferably a pharmaceutically acceptable excipient and other additives if necessary.

Pharmaceutically acceptable excipients are commonly known in the state of the art and are described for example in the treatise by Kibbe A. (2000), "*Handbook of Pharmaceutical Excipients*", Third Edition, American Pharmaceutical Association and Pharmaceutical Press. Additives comprise, according to the invention, any compound or composition that is advantageous for therapeutic application, and includes salts, binders, as well as other active substances.

Another object relates to a kit, comprising the monoclonal antibody according to the invention or fragments thereof.

Provision of the antibody according to the invention in such a kit, optionally together with other reagents, buffers, and instructions on how to use the antibody, has the advantage that application is greatly simplified and for example in hospitals and large laboratories, in which semiskilled personnel sometimes work, safety is created.

It is to be understood that the features stated above and those that are to be presented below can be used not only in the combination stated, but also in other combinations or on their own, while remaining within the scope of the present invention.

The present invention will now be explained in more detail on the basis of embodiments of application, which are purely illustrative and do not in any way limit the scope of the present invention. Reference is to be made to the appended drawing.

BRIEF DESCRIPTION OF THE DRAWING

FIG. 1 FACS histograms for the reactivity of the antibodies CH3A4A7 (A), W3D2B10 (B) and W3C4E11 (C).

EMBODIMENT

Production of Transfectants cDNAs encoding FZD-4, -7 and -9 were produced. These were cloned into the cloning vector pIRES-EGFP (Becton and Dickinson Biosciences, Franklin Lakes, N.J., USA) in accordance with the manufacturer's instructions. A flag-TAG was inserted at the N-terminal end, in order to demonstrate that the FZD receptors are membrane-bound. HEK-293 cells (DSMZ No. ACC 305) were transfected with these pIRES-EGFP constructs.

The transfected HEK-293 cells were separated by gel electrophoresis, and the proteins were transferred to a nitrocellulose membrane. Then Western blots were carried out with antisera-containing polyclonal antibodies against FZD-4, -7 and -9 (Acris Antibody GmbH, 32120 Hiddenhausen, Germany). It was found that all the transfectants express the desired FZD constructs (data not shown).

One week after transfection, the cells were labeled with an anti-flag antibody and a PE-conjugated anti-mouse antibody, and the EGFP- and flag-positive cells were sorted in a FACS sorter over several rounds, until a transfectant was generated that was strongly positive for EGFP and flag. As a rule a stable transfectant could be produced after three to four sorting cycles.

Immunization

The transfectants obtained as described previously were used for the immunization of Balb/c mice (i.p.). After four immunizations at intervals of 14 days, fusion of spleen cells with the myeloma line SP2/0 was carried out.

Immunization can also be carried out with the human neuroblastoma cell line CHP-126 (DSMZ No. ACC 304), in order to obtain antibodies against human FZD-4, and with the human retinoblastoma cell line WER1-RB-1 (DSMZ No. ACC 90), to obtain antibodies against human FZD-7 or FZD-9 or FZD-6. These cells display high expression of the respective FZD receptors. In each case $10^7$ cells are used.

Hybridoma supernatants, which reacted with the transfectants or previously with the CHP-126 or WER1-RB-1 cells, but not with the wild-type or control cells, were selected and the corresponding hybridomas were cloned. Positive clones were selected.

Four clones were obtained in this way. These were designated CH3A4A7 which secrets monoclonal antibodies against FZD-4, W3D2B10 which secrets monoclonal antibodies against FZD-7, and W3C4E11 which secrets the monoclonal antibodies against FZD-9 or FZD-6. The antibodies have the following isotypes: CH3A4A7 and W3D2B10 each have mouse IgG1, W3CH411 mouse IgM.

Analysis of the Reactivity of the Antibodies on Defined Stem Cell Populations

The antibodies obtained as described previously were tested for their reactivity on defined stem cell populations. The results of these investigations are presented in Table 1 below.

TABLE 1

Reactivity of the antibodies according to the invention with various cell types.
The various cell types are tumor cell lines (*), primary cells (+), cultivated primary cells (°), leukemia cells (☉)

| Cell type | Antibody | | |
|---|---|---|---|
| | CH3A4A7 (anti-FZD-4-mab) | W3C4E11 (anti-FZD-9-mab) | W3D2B10 (anti-FZD-7-mab) |
| Calu-1* | nd | − | − |
| T-47D* | + | − | − |
| A172* | + | − | − |
| NCH-H69* | (+) | − | (+) |
| DU-4475* | − | − | − |
| JEG-3* | + | − | − |
| MCF-7* | + | − | − |
| Weri-Rb-1* | + | + | + |
| NT-2* | + | + | − |
| 293E* | − | − | − |
| CHP-126* | + | (+) | − |
| HELA* | − | − | − |
| SK-Lu-1* | (+) | − | − |
| PB+ | − | − | − |
| BM+ | − | − | − |
| CD34 + BM+ | − | − | − |
| NPC+ | + | − | − |
| MSC° | nd | − | − |
| HUVEC° | − | − | − |
| EM-20° | − | − | − |
| HL-60° | − | − | − |
| KG-1° | − | − | − |
| KG-1a° | − | − | − |
| U266° | − | − | + |
| Nalm-1° | (+) | − | − |
| Reh° | − | − | + |
| BV-173° | nd | − | − |

TABLE 1-continued

Reactivity of the antibodies according to the invention with various cell types.
The various cell types are tumor cell lines (*), primary cells (+), cultivated primary cells (°), leukemia cells (⊙)

| | Antibody | | |
|---|---|---|---|
| Cell type | CH3A4A7 (anti-FZD-4-mab) | W3C4E11 (anti-FZD-9-mab) | W3D2B10 (anti-FZD-7-mab) |
| CML-T1⊙ | − | + | + |
| MO7-e⊙ | − | − | − |
| MOLM-1⊙ | − | − | − |
| HEL⊙ | − | − | − |
| KU-812⊙ | − | − | − |
| UT-7⊙ | − | − | − |
| MEG-O1 | − | − | − |
| TF-1⊙ | − | − | − |
| K562⊙ | − | − | − |
| U937⊙ | − | − | − |
| CCRF-CEM⊙ | − | − | − |

Information about the individual cell types can be found on the website of the "Deutsche Sammlung für Mikroorganismen und Zellkulturen" (DSMZ). The contents of the descriptions of the listed cell types are incorporated in the present application by reference. NPC stands for neuronal progenitor cells, MSC for mesenchymal stem cells, BM for bone marrow, CD34$^+$BM for CD34-positive BM cells (stem cells), PB for peripheral blood cells and HUVEC for human umbilical vein endothelial cells.

It was found that a great many tumor cells express FZD receptors and these cells can be specifically selected and optionally isolated with the provided antibodies.

Extracts from the relevant FACS printouts are shown in FIG. 1. FIG. 1A shows the reaction profile of the antibody CH3A4A7 in the form of FACS histograms or FACS printouts against HEK-293 wild-type cells (HEK-293), against the transfectants (HEK-293/FZD-4), against neuronal progenitor cells (NPC), against mobilized peripheral blood (mPB), against bone marrow cells (BM) and against mesenchymal stem cells (MSC). In addition, it was verified, using an anti-flag antibody (a-flag), that the respective Frizzled protein is expressed in the membrane. FIG. 1B shows the corresponding histograms for the W3D2B10 antibody, and FIG. 1C shows the corresponding histograms for the W3C4E11 antibody. The FACS analyses were preformed according to standard methods, as described for example in DE 102 42 337 A1, the contents of which is incorporated into the present application by reference.

Figure 1A:
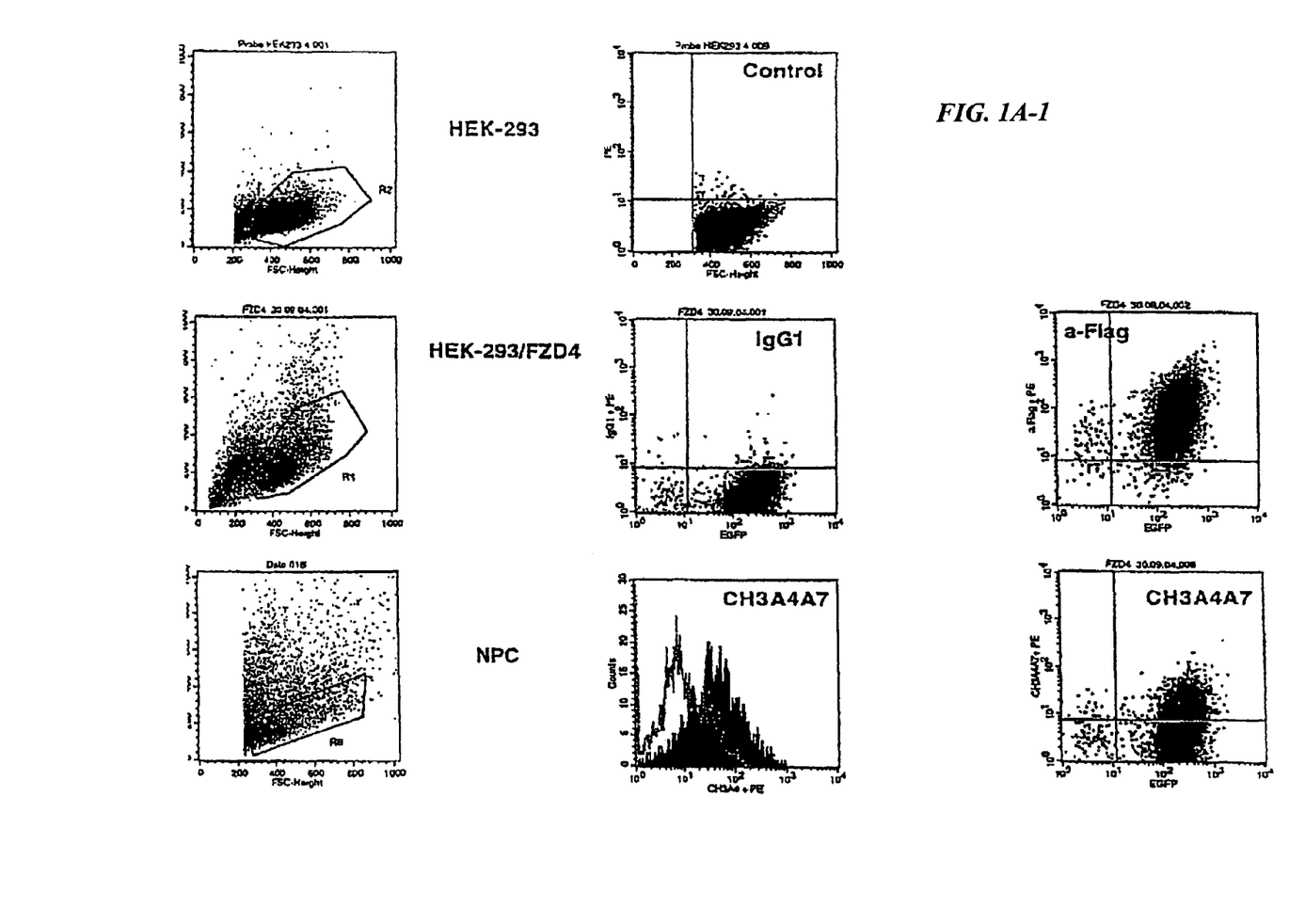
Figure 1A:
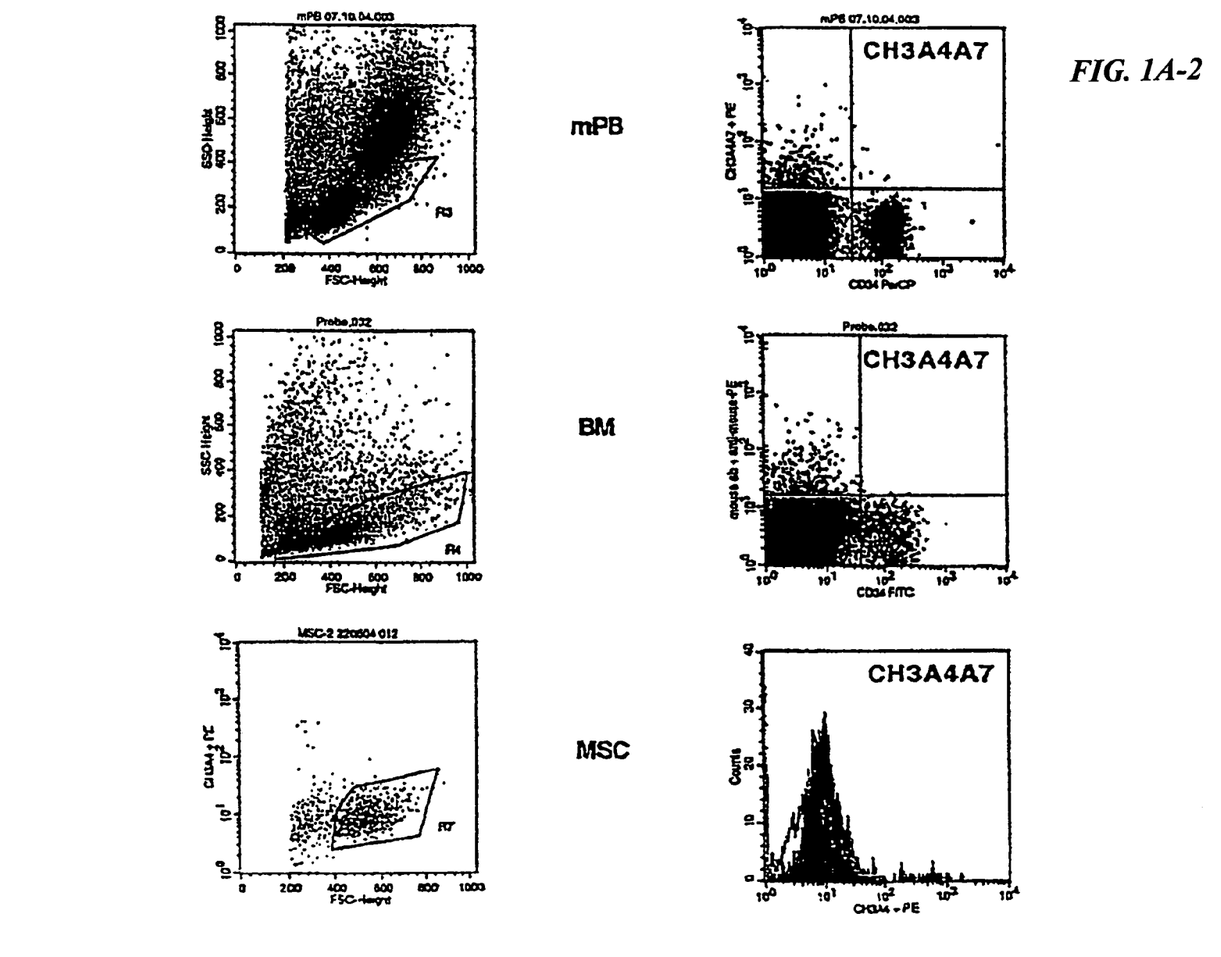
Figure 1B:
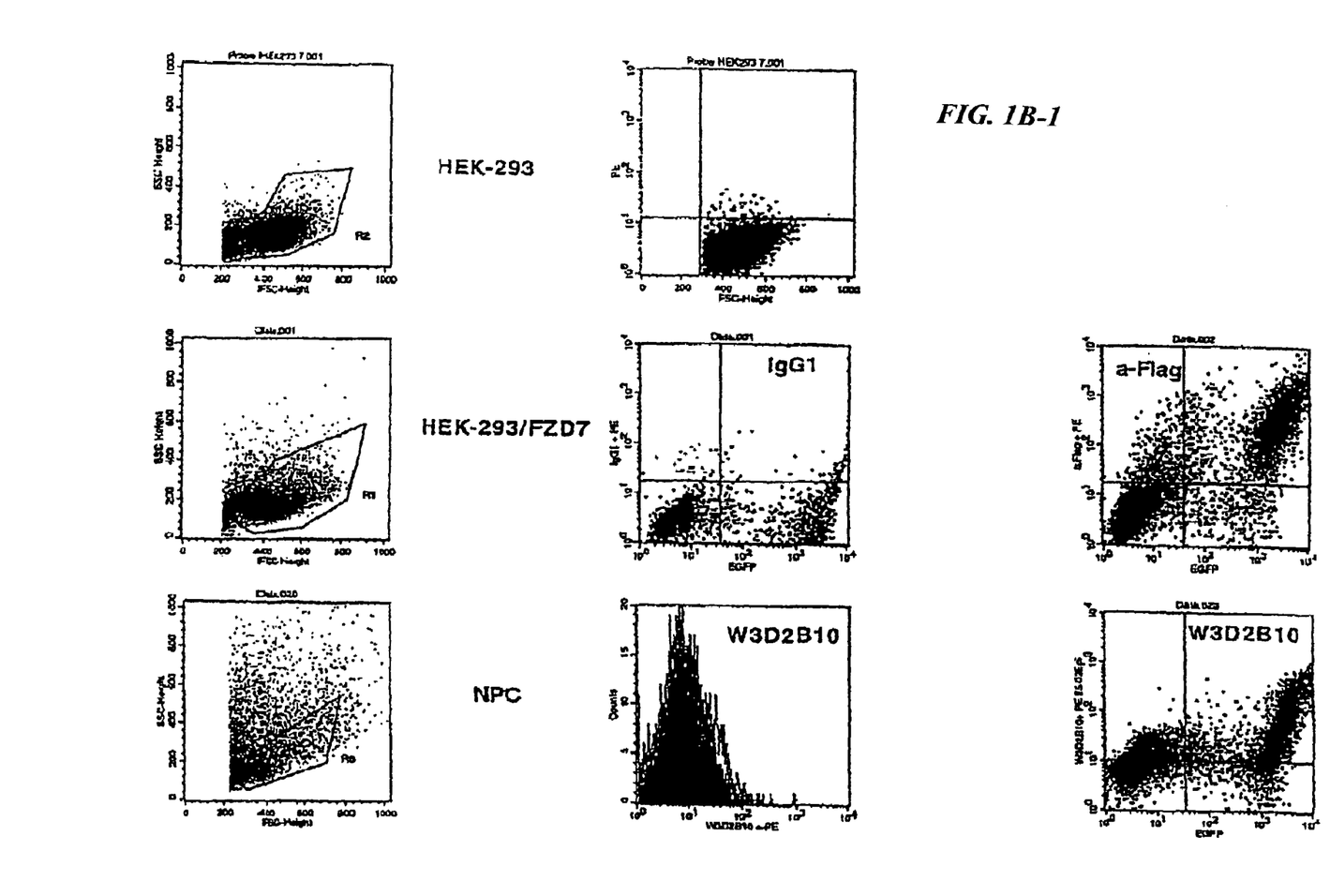
Figure 1B:
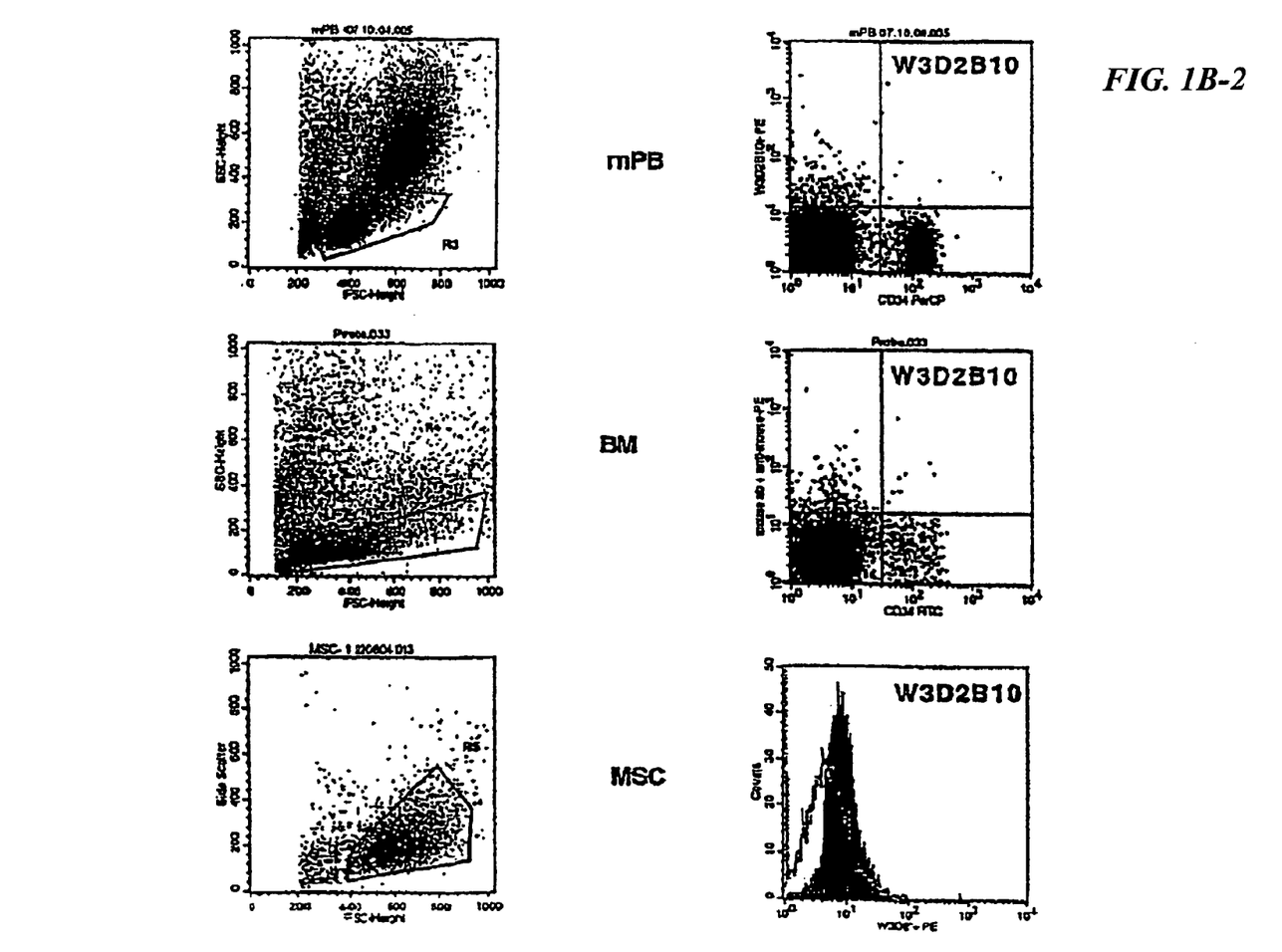
Figure 1C:
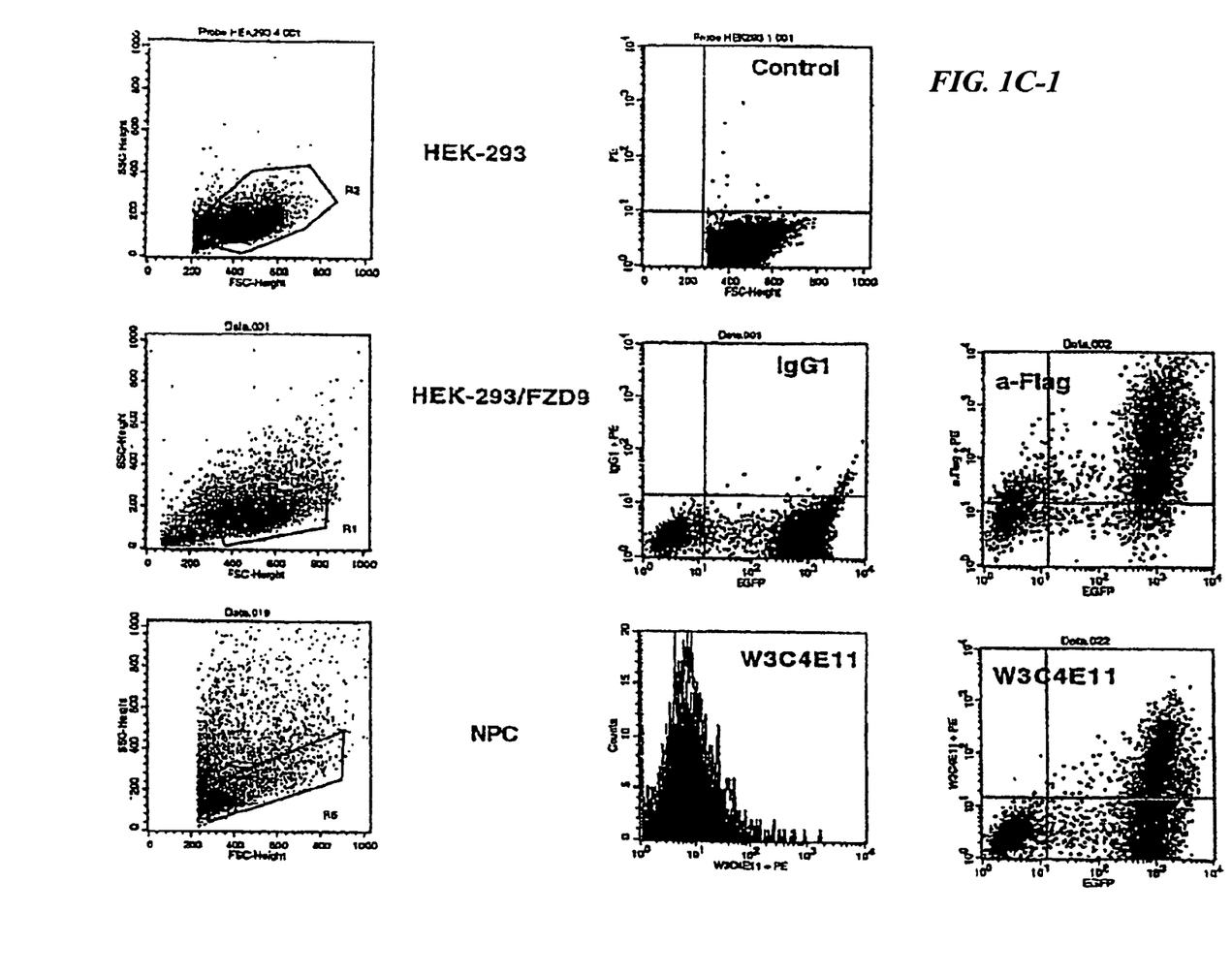
Figure 1C:
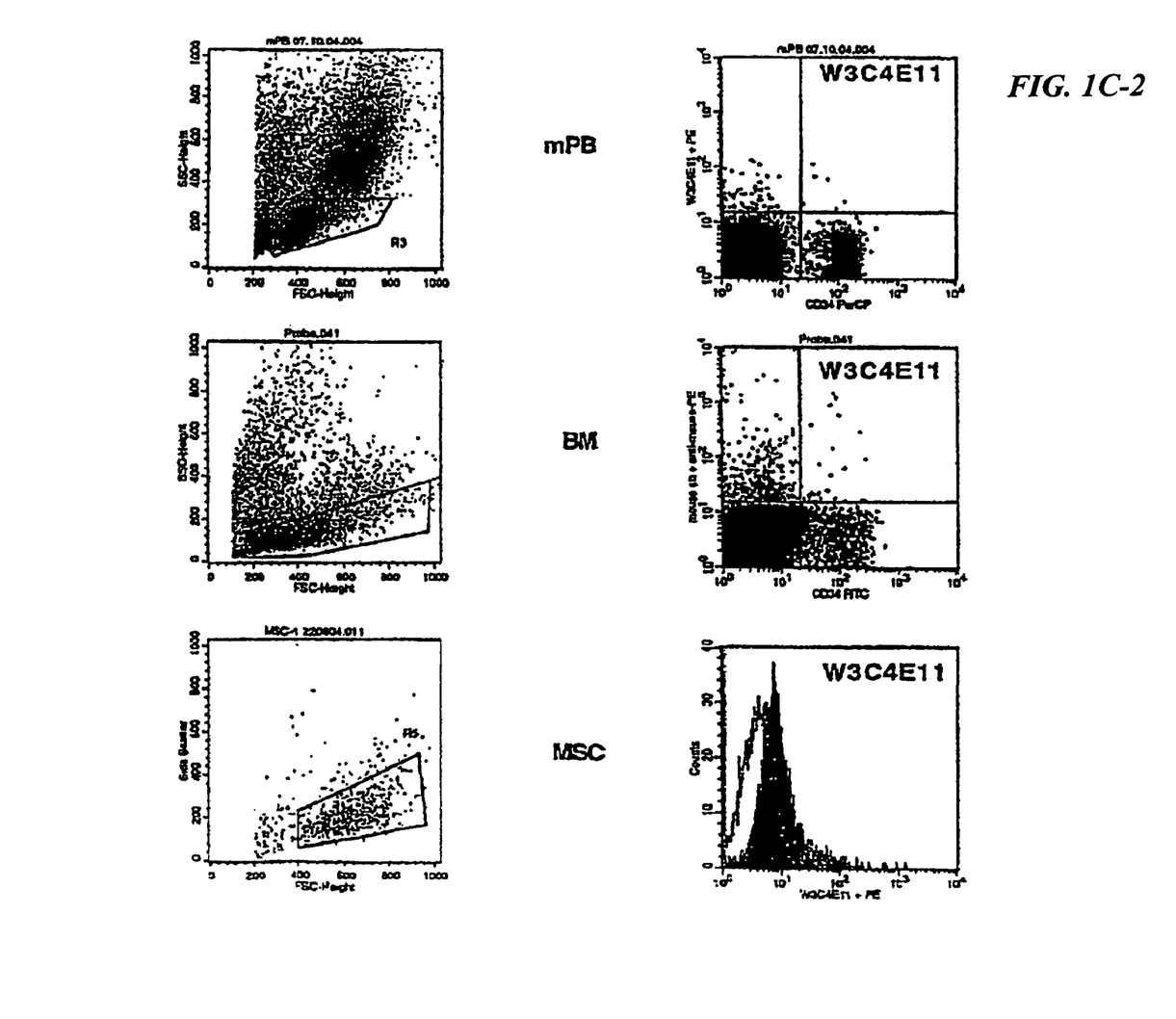

In particular it was found that the monoclonal antibody that is secreted by the clone CH3A4A7 only recognizes, highly specifically and selectively, transfectants that were transfected with the FZD-4 construct [FIG. 1A (HEK-293/FZD4) and data not shown]. The same applies correspondingly with respect to FZD-7 for the antibody that is secreted by clone W3D2B10. The latter only recognizes highly specifically and selectively those HEK-293 transfectants that were transfected with the FZD-7 construct [FIG. 1B (HEK-293/FZD7) and data not shown]. Moreover, the monoclonal antibody that is secreted by clone W3C4E11 only recognizes highly specifically and selectively those HEK-293 transfectants that were transfected with the FZD-9 construct [FIG. 1C (HEK-293/FZD9) and data not shown].

The antibodies according to the invention are therefore highly selective and specific.

Use of the Antibodies

The antibodies according to the invention are used in accordance with usual practice, for example in Western blotting, immunoprecipitation or other immunological techniques. For this, the antibodies are used in the customary buffers, for example Tris or HEPES buffers, at the desired concentration, which can easily be determined for example by titration experiments. Further details about the use of the antibodies according to the invention can be found in standard works on molecular biology, for example the work by Ed Harlow and David Lane (1998), "*Using Antibodies: A Laboratory Manual*", Cold Spring Harbor Laboratory Press, the content of which is incorporated into the present application by reference.

The inventors have, for the first time, prepared monoclonal antibodies that recognize human variants of the FZD receptors highly specifically and highly selectively. Said antibodies are extremely valuable tools, which can be used both in basic research and in diagnostics and pharmaceutics.

The invention claimed is:

1. A monoclonal antibody or a fragment thereof that binds specifically an to a human receptor of the Frizzled (FZD) family, wherein said antibody or fragment thereof binds to an identical antigen as an antibody that is produced by the hybridoma cells that were deposited in culture CH3A4A7 at the Deutsche Sammlung für Mikroorganismen und Zellkulturen (DSMZ), under number DSM ACC 2667 in accordance with the Budapest Treaty.

2. A monoclonal antibody or fragment thereof that binds specifically to a human receptor of the Frizzled (FZD) family, wherein said antibody or fragment thereof is produced by the hybridoma cell that was deposited in culture CH3A4A7 at the DSMZ under number DSM ACC 2667.

3. The monoclonal antibody or fragment thereof as claimed in claim 1, wherein a marker and/or a therapeutic active substance is coupled to it.

4. A hybridoma cell that produces the antibody or fragment thereof as claimed in claim 1, wherein the hybridoma is deposited as culture CH3A4A7 at the Deutsche Sammlung für Mikroorganismen und Zellkulturen (DSMZ), under number DSM ACC 2667 in accordance with the Budapest Treaty.

5. A composition comprising the monoclonal antibody or fragment thereof as claimed in claim 1 and a pharmaceutically acceptable excipient and optionally other additives.

6. A kit comprising the monoclonal antibody or fragment thereof as claimed in claim 1 and instructions on how to use the antibody.

7. A method for the detection and/or isolation of a human receptor of the FZD family or fragments thereof in a biological sample, wherein the human receptor is FZD-4, comprising the following steps:
 (1) provision of said biological sample;
 (2) contacting said biological sample with an antibody or fragment thereof;
 (3) determination whether specific binding to said antibody or fragment thereof has taken place, and
 (4.1) correlation of a positive result in step (3) with the detection of a receptor from the FZD family, and/or
 (4.2) isolation of the antigen in the case of a positive result in step (3),
 wherein the antibody or the fragment thereof as claimed in claim 1 is used as said antibody or said fragment.

8. A method for the identification of biological sample with respect to the presence and/or expression of a receptor of the FZD family or fragments thereof and optionally isolation of said material, wherein the receptor is FZD-4, comprising the following steps:
(1) provision of said biological sample;
(2) contacting said biological sample with an antibody or fragment thereof;
(3) determination whether specific binding to said antibody or fragment thereof has taken place, and
(4.1) correlation of a positive finding in step (3) with the identification of the presence and/or expression of a receptor of the FZD family or fragments thereof in or on the biological sample, and optionally
(4.2) isolation of the binding partner of said antibody or fragment thereof if the determination in step (3) is positive,
wherein the antibody or the fragment thereof as claimed in claim 1 is used as said antibody or said fragment thereof.

* * * * *